US007323586B2

(12) United States Patent
Wiese et al.

(10) Patent No.: US 7,323,586 B2
(45) Date of Patent: Jan. 29, 2008

(54) PHTHALIC ACID ALKYL ESTER MIXTURES WITH CONTROLLED VISCOSITY

(75) Inventors: Klaus-Diether Wiese, Haltern am See (DE); Michael Grass, Haltern am See (DE); Wilfried Bueschken, Haltern am See (DE)

(73) Assignee: Oxeno Olefinchemie GmbH, Marl (DE)

( * ) Notice: Subject to any disclaimer, the term of this patent is extended or adjusted under 35 U.S.C. 154(b) by 0 days.

(21) Appl. No.: 10/487,061

(22) PCT Filed: Sep. 20, 2002

(86) PCT No.: PCT/EP02/10570

§ 371 (c)(1),
(2), (4) Date: Feb. 18, 2004

(87) PCT Pub. No.: WO03/029180

PCT Pub. Date: Apr. 10, 2003

(65) Prior Publication Data

US 2004/0238787 A1 Dec. 2, 2004

(30) Foreign Application Priority Data

Sep. 26, 2001 (DE) ................. 101 47 567
Jan. 16, 2002 (DE) ................. 102 01 348

(51) Int. Cl.
C07C 67/08 (2006.01)
C07C 67/10 (2006.01)
C07C 69/76 (2006.01)
C09K 3/00 (2006.01)

(52) U.S. Cl. .................. 560/98; 560/76; 106/316; 524/296; 524/297; 252/182.28

(58) Field of Classification Search .................. 560/98
See application file for complete search history.

(56) References Cited

U.S. PATENT DOCUMENTS

| 2,362,767 | A | * | 11/1944 | Morgan ...................... 508/482 |
| 2,517,351 | A | * | 8/1950 | Reid .......................... 524/296 |
| 2,517,352 | A | * | 8/1950 | Reid .......................... 524/287 |
| 2,610,201 | A | * | 9/1952 | Rutherford .................. 560/76 |
| 2,792,417 | A | * | 5/1957 | Dean .......................... 560/76 |
| 3,281,456 | A | * | 10/1966 | Renchhoff et al. ............ 560/85 |
| 4,291,127 | A | * | 9/1981 | Akabayashi et al. .......... 560/76 |
| 4,426,542 | A | * | 1/1984 | Barker et al. ................ 568/883 |
| 4,728,540 | A | * | 3/1988 | Gasman .................... 427/385.5 |
| 6,015,928 | A |   | 1/2000 | Gubisch et al. |
| 6,184,424 | B1 |   | 2/2001 | Bueschken et al. |
| 6,239,318 | B1 |   | 5/2001 | Schuler et al. |
| 6,307,093 | B1 | * | 10/2001 | Godwin et al. ............. 560/129 |
| 6,331,657 | B1 |   | 12/2001 | Kaizik et al. |
| 6,403,836 | B2 |   | 6/2002 | Kaizik et al. |
| 6,407,295 | B1 |   | 6/2002 | Kaizik et al. |
| 6,433,242 | B1 | * | 8/2002 | Wiese ....................... 585/800 |
| 6,437,170 | B1 | * | 8/2002 | Thil et al. ..................... 560/76 |
| 6,482,992 | B2 |   | 11/2002 | Scholz et al. |
| 6,492,564 | B1 |   | 12/2002 | Wiese et al. |
| 6,500,991 | B2 |   | 12/2002 | Wiese et al. |
| 6,555,716 | B2 |   | 4/2003 | Protzmann et al. |
| 6,570,033 | B2 |   | 5/2003 | Rottger et al. |
| 6,627,782 | B2 |   | 9/2003 | Kaizik et al. |
| 6,680,414 | B2 |   | 1/2004 | Knoop et al. |
| 6,720,457 | B2 |   | 4/2004 | Drees et al. |
| 6,818,770 | B2 |   | 11/2004 | Selent et al. |
| 6,924,389 | B2 |   | 8/2005 | Jackstell et al. |
| 6,956,133 | B2 |   | 10/2005 | Jackstell et al. |
| 6,960,699 | B2 |   | 11/2005 | Totsch et al. |
| 7,009,068 | B2 |   | 3/2006 | Schmutzler et al. |
| 7,109,346 | B2 |   | 9/2006 | Beller et al. |
| 2004/0015007 | A1 | * | 1/2004 | Grass et al. ................ 560/103 |
| 2004/0236133 | A1 |   | 11/2004 | Selent et al. |
| 2004/0238787 | A1 | * | 12/2004 | Wiese et al. ........... 252/182.28 |
| 2004/0242947 | A1 |   | 12/2004 | Beller et al. |
| 2005/0043279 | A1 |   | 2/2005 | Selent et al. |
| 2005/0182277 | A1 |   | 8/2005 | Totsch et al. |

(Continued)

FOREIGN PATENT DOCUMENTS

DE 199 18 051 10/2000

(Continued)

OTHER PUBLICATIONS

USPTO obtained translation of EP 424767-A2, (May 2, 1991) Hoffman et al.*

(Continued)

Primary Examiner—Joseph D. Anthony
(74) Attorney, Agent, or Firm—Oblon, Spivak, McClelland, Maier & Neustadt, P.C.

(57) ABSTRACT

Mixtures of isomeric dialkyl phthalates that have a desired viscosity are prepared by esterifying phthalic acid or phthalic anhydride with a mixture of isomeric alkyl alcohols having a certain carbon number of carbon atoms, where the molar fraction of each alkyl alcohol isomer of the isomeric alcohol mixture is determined, and where the viscosity parameter of each alkyl alcohol isomer of the alcohol mixture, which, upon reacting with phthalic acid or phthalic anhydride, results in a mixed isomer dialkyl phalate ester product having a specific desired viscosity, is determined in accordance with formula (I):

$$\ln(\eta) = \Sigma \chi_i * \ln(\eta_i) \qquad (I)$$

where η=the calculated viscosity of a dialkyl phthalate mixture, $\chi_i$=the molar fraction of an isomerically pure alcohol (i), and $\eta_i$=the viscosity parameter of isomerically pure alcohol (i).

26 Claims, No Drawings

U.S. PATENT DOCUMENTS

| | | |
|---|---|---|
| 2005/0209489 A1 | 9/2005 | Moller et al. |
| 2005/0234270 A1 | 10/2005 | Kaizik et al. |
| 2005/0256281 A1 | 11/2005 | Grund et al. |
| 2006/0036121 A1 | 2/2006 | Kaizik et al. |
| 2006/0128998 A1 | 6/2006 | Lueken et al. |
| 2006/0129004 A1 | 6/2006 | Lueken et al. |
| 2006/0161017 A1 | 7/2006 | Grass et al. |
| 2006/0183936 A1 | 8/2006 | Grass et al. |
| 2006/0241324 A1 | 10/2006 | Moeller et al. |

FOREIGN PATENT DOCUMENTS

| | | |
|---|---|---|
| EP | 278407 A2 * | 8/1988 |
| EP | 424 767 | 5/1991 |
| EP | 1 029 839 | 8/2000 |
| WO | 00/63151 | 10/2000 |

OTHER PUBLICATIONS

U.S. Appl. No. 11/494,741, filed Jul. 28, 2006, Kaizik, et al.
U.S. Appl. No. 10/562,454, filed Aug. 18, 2006, Krissmann, et al.
U.S. Appl. No. 10/576,302, filed Apr. 19, 2006, Kaizik, et al.
U.S. Appl. No. 10/588,762, filed Aug. 8, 2006, Wiese, et al.
U.S. Appl. No. 10/593,330, filed Sep. 19, 2006, Borgmann, et al.
U.S. Appl. No. 10/584,492, filed Jun. 22, 2006, Ortmann, et al.
U.S. Appl. No. 10/584,148, filed Jun. 22, 2006, Ortmann et al.
U.S. Appl. No. 11/574,063, filed Feb. 22, 2007, Nierlich, et al.

* cited by examiner

PHTHALIC ACID ALKYL ESTER MIXTURES WITH CONTROLLED VISCOSITY

The invention relates to mixtures of phthalic esters whose viscosity can be adjusted via the contributions of each of the isomeric alcohols from which the phthalic esters can be prepared, and to their use.

BACKGROUND

Phthalic esters are widely used as plasticizers for plastics, such as PVC. Plasticizers may be defined as substances which give a material, in particular plastics, increased flexibility, softness, and processability (Alan S. Wilson, Plasticizers, The Institute of Materials, 1995, ISBN 0 901716 76 6, p. 1). The plasticizing of PVC is of particular, although not exclusive, interest.

For over 100 years there has been constant development of new plasticizers, almost always using polyfunctional esters. The esters most frequently used are those of polybasic carboxylic acids and monoalcohols. Examples of polybasic aromatic carboxylic acids or their anhydrides which are used are phthalic acid and isophthalic acid, trimellitic acid, pyromellitic acid, and terephthalic acid. Inorganic acids are also used, the best known example being phosphoric esters. These carboxylic acids or their anhydrides, or in the case of the phosphoric esters also the acid chlorides, such as $POCl_3$, are generally reacted with monoalcohols, such as ethanol, butanol, isobutanol, n-amyl alcohol, isoamyl alcohol, heptanol, 2-ethylhexanol, or 2-propylheptanol. The higher alcohols used preferably include isomer mixtures which are obtained by oligomerizing olefins having from 3 to 5 carbon atoms, with subsequent hydroformylation and hydrogenation of the resultant aldehydes. Industrial examples are isoheptanol, isooctanol, isononanol, isodecanol, and isotridecanol. Oligomerization of ethylene also gives access to linear compounds known as alpha-olefins, which on hydroformylation give a mixture of linear alcohols and alcohols with a low degree of branching. Examples of alcohols prepared industrially in this way are nonanol and undecanol and mixtures of these. Straight-chain alcohols are accessible from the chemistry of fats, or else via synthetic routes which increase molecular weight and start from ethylene, examples being those known as the Ziegler alcohols. Finally, mention may also be made of cyclic alcohols, such as cyclohexanol, benzyl alcohol, phenols, cresols, and xylols, which have been used industrially.

It is also possible to use the opposite approach, reacting polyhydric alcohols with monocarboxylic acids to give plasticizers, rather than polybasic carboxylic acids with monoalcohols. Examples of polyhydric alcohols are neopentyl glycol, trimethylolpropane, pentaerythritol, dipentaerythritol, ethylene glycol and its oligomers di-, tri- and tetraethylene glycol, glycerol, butanediol, hexanediol, etc. Sugar alcohols have also been used for this purpose. The carboxylic acids used here are compounds analogous to the abovementioned alcohols, i.e. carboxylic acids in the range from 2 to about 13 carbon atoms. Examples are acetic acid in triacetin, butyric acids, valeric acids, heptanoic acid, nonanoic acid, and also isomer mixtures, such as isoheptanoic, isooctanoic, isononanoic, isodecanoic, and isotridecanoic acid.

It is also possible to use compounds which have both an acid function and an alcohol function. The best known example is citric acid, which has three carboxylic acid groups and one alcohol group. Esterification of the carboxylic acid groups with monoalcohols gives useful esters, and the alcohol group may then also be esterified with a carboxylic acid, such as butyric acid or acetic acid.

For the sake of completeness mention should be made of the fact that esters of monoalcohols and monocarboxylic acids are also used as plasticizers in specific cases if their boiling point is sufficiently high, examples being stearic or lauric esters.

The above list is not fully comprehensive, however. For example, combinations of polyhydric alcohols with polybasic carboxylic acids have also been used as plasticizers. An example is the linkage of diols and dicarboxylic acids to give low-molecular-weight polyesters, the end groups of which are then esterified using monofunctional alcohols or carboxylic acids. The remaining alcohol groups are then in turn esterified using monocarboxylic acids. Use can also be made of ether bonds to increase the number of esterifiable groups, as in di- and tripentaerythritol, which have 6 and, respectively, 8 esterifiable alcohol groups. This method is used especially when particularly high-molecular-weight plasticizers with high polar content are desired.

Very generally, the aim is to prepare compounds which have sufficient polarity to serve as good plasticizers, have high molar mass in order to have the lowest possible volatility, and exhibit little migration within the material, but are nevertheless liquid and have low viscosity in relation to their molar mass, so that they are easy to process.

Mention should also be made of the fact that compounds or mixtures of compounds which have these properties also have important other application sectors, for example as synthetic lubricants, hydraulic fluids, and also as solvents in ointments, inks, etc. The term functional fluids is often used.

Using the method described above it is possible to tailor esters for almost every conceivable use, but of course there are limits imposed by the resources required and the costs associated therewith, and also by the availability of the raw materials. Many of the possible combinations listed have therefore now disappeared from the market, or have achieved only limited significance in niche applications, or are of merely academic interest. However, the situation can sometimes change rapidly when new processes provide access to low-cost raw materials, or changes in attitude to the environment require that replacements are found for products commonly used hitherto, or new technical requirements demand new solutions.

For the sake of simplicity, the descriptions below are restricted to a few selected examples of particular industrial relevance from the PVC plasticizers application sector. However, the problems described below and their solution are transferable in principle to all of the esters mentioned.

Problems

Easily the most important class of esters for plasticizers is the phthalates. Within these, it is then 2-ethylhexyl (also often known by the abbreviated term "octyl") phthalate, DOP (dioctyl phthalate) or DEHP (diethylhexyl phthalate), which currently predominate. However, it is increasingly being displaced by DINP (diisononyl phthalate), which has marked performance advantages, such as lower volatility and less migration. Unlike DEHP which, apart from stereoisomers, is a single chemically defined substance with unambiguously determinable properties, DINP is a mixture of many similar isomers of identical molar mass. This is a result of the origin of the isononanol used for the esterification process.

Isononanol is prepared by hydroformylating octenes, which in turn are produced in various ways. The raw material generally used is industrial $C_4$ streams which initially comprise all of the isomeric $C_4$ olefins alongside saturated butanes and, in some cases, contaminants, such as $C_3$ and $C_5$ olefins and acetylenic compounds. Extractive distillation is first used to obtain the useful compound butadiene, for example using NMP (N-methylpyrrolidone). As an alternative, the butadiene may also be converted via selective hydrogenation into 1- and 2-butene, e.g. as in the SHP-CB process of OXENO GmbH. In both cases the product is a $C_4$ stream in which the only olefins substantially still present are isobutene and 1- and 2-butene, often termed "raffinate I". Oligomerization of this olefin mixture gives mainly octenes, alongside higher oligomers, such as $C_{12}$ and $C_{16}$ olefin mixtures. The $C_8$ cut is called "codibutylene" and was previously used for preparing isononanols for plasticizers.

Nowadays, the isobutene is generally removed in a second step of the process by reaction with methanol with acidic catalysis, for example using acidic ion exchangers. This gives the important fuel additive methyl tert-butyl ether (MTBE) and a $C_4$ stream known as "raffinate II" and substantially free from isobutene. It is also possible to use other alcohols, such as ethanol, instead of methanol. In that case ethyl tert-butyl ether, ETBE, is obtained. Selective removal of isobutene is also possible using water instead of alcohols, with formation of tert-butyl alcohol TBA, which again is an important compound utilized by industry. Cleavage of the TBA in a reverse reaction gives high-purity isobutene. In all of the variants discussed, there remains a $C_4$ stream in which the only substantial materials still present are 1- and 2-butene alongside the saturated butanes, known as "raffinate II".

The useful material 1-butene may optionally be obtained from raffinate II, for example as a comonomer for polyolefins, as can isobutane, which is used as a fuel gas. This then gives a $C_4$ stream impoverished with respect to 1-butene, raffinate III. Either raffinate II or raffinate III may be used as raw material for oligomerization. Here again, there are various approaches utilized industrially. The older oligomerization processes operate with acidic catalysts, such as phosphoric acid, on supports, or acidic zeolites (process variant A). The products here are octenes, essentially consisting of dimethylhexenes. Newer processes, such as the DIMERSOL process, operate with soluble Ni complex catalysts. These give octene mixtures with high proportions of 3- and 5-methylheptenes alongside n-octenes and dimethylhexenes (process variant B). The most modern processes utilize the high selectivity of specific supported Ni catalysts, the OCTOL process from OXENO GmbH being well known. The octene mixtures obtained here have the least branching, a particularly useful factor for plasticizer alcohol applications (process variant C). The table below gives only approximate values for the composition of each of the products obtained, since the precise composition depends on the catalyst, temperature, residence time, degree of conversion, and other conditions employed. However, it can clearly be seen that the isomer compositions obtained differ depending on the process. Raffinate II or III gives

|  | A acidic catalysis | B Dimersol | C Octol |
| --- | --- | --- | --- |
| n-octenes | 0% | 6% | 13% |
| methylheptenes | 5% | 59% | 62% |
| dimethylhexenes | 70% | 34% | 24% |
| others | 25% | 1% | 1% |

Another way of obtaining octenes is the oligomerization of isobutene. The main product here is a mixture of 2,4,4-trimethyl-1-pentene and 2,4,4-trimethyl-2-pentene. An oligomerization of ethylene with Ziegler catalysis or by the SHOP process is another route to higher olefins, forming linear terminal olefins with broad carbon number distribution. A $C_8$ cut, inter alia, may be obtained here, and these cuts are also available from Fischer-Tropsch processes. Finally, the opportunity is occasionally utilized of isolating hydrocarbons of suitable carbon number from naphtha streams. These comprise mainly saturated alkanes, which are converted to olefins by dehydrogenation.

An entirely different method is the oligomerization of crude unseparated olefin streams, such as those arising during cracker processes, e.g. cuts which comprise $C_3$, $C_4$, and, where appropriate, $C_5$ olefins. Under acidic oligomerization these streams give a mixture of all conceivable combinations of these olefins, i.e. hexenes, heptenes, octenes, nonenes, decenes, etc., and these are broken down into carbon number cuts, known as polygas olefins. The main products obtained here are relatively highly branched internal olefins.

Overall, there is a wide variety of processes which give olefins of suitable chain length for the oxo reaction/hydrogenation to give plasticizer alcohols. Depending on the process, the isomer mixtures obtained have very different degrees of branching—from unbranched to triply or multiply branched, and have various double bond positions from terminal to almost exclusively internal.

The next step in the process after oligomerization is hydroformylation, i.e. reaction of the olefins with carbon monoxide and hydrogen, known as synthesis gas, to give aldehydes. Here again use is made of a number of industrial variants. Hydroformylation with the catalyst hydridocobalt carbonyl at from 200 to 300 bar and from 170 to 190° C. is commonly used (high-pressure Co process, HPCo). Co catalysts modified with alkyl-phosphines are also used industrially (Co ligand). Another known process operates with rhodium instead of cobalt as catalyst at from 100 to 300 bar and from 120 to 130° C. (HPRh). The three processes differ markedly in the isomeric composition of the products. For example, the HPCo oxo reaction of internal linear octenes gives about 50% of linear n-nonanol alongside the internal isomers from the oxo reaction (n/i~1), while the oxo reaction using ligand-modified Co gives about 80% (n/i~4), and the HPRh oxo reaction gives about 20% (n/i~0.25). Similar considerations also apply to the oxo reaction of branched olefins.

It should also be mentioned that even though the empirical formula is the same, e.g. $C_8H_{16}$ for octenes, the olefin cuts used industrially comprise very different structural and double-bonding isomers. Even when an identical olefin cut is used, the degree of branching in the plasticizer alcohols obtained via oxo reaction/hydrogenation varies widely as a function of the oxo process used. And even where there is a fixed combination of one oligomerization process with one oxo process, variations in isomer composition occur as a result of variations in composition of the raw materials used, such as $C_4$ cut, deriving from variations in operating conditions, from adjustment of conversion to the required production program, and from many other factors.

The isomer composition of the plasticizer alcohols produced may therefore vary within wide limits. However, it is known that the physical properties and performance of plasticizers are highly dependent on their structure. As an example of a physical property, the viscosity of phthalates measured at 20° C. is given below. Specifically, phthalates of isononanol (DINPs), can have viscosities in the range from 50 to 60 mPa*s where linear olefins are used, but there are also known DINP grades with from 160 to 170 mPa*s where codibutylene is used. DINP grades based on polygas octenes have viscosities in the range from 90 to 110 mPa*s. Using raffinate II or III with the octol process, the alcohols obtained have phthalates with viscosities in the range from 72 to 82 mPa*s if the oxo reaction used is the high-pressure Co process. Using Rh catalysts the same starting material gives plasticizers with from 90 to 100 mPa*s.

The remarks below are essentially restricted to some variants of plasticizers based on octenes, but the skilled worker will readily appreciate that the problems are present wherever mixtures, and in particular isomer mixtures, are used to prepare esters which are functional fluids, plasticizers being regarded here as a subgroup of functional fluids.

The performance needed by an ester to fulfill its function is exceptionally complex. For use as a lubricant, for example, viscosity, drop point, dependence of viscosity on temperature, and many other factors play a part. Factors for plasticizers are not only flexibilizing action, in particular at low temperatures, but also plasticizer viscosity and, for use in cable sheathings, electrical properties. All of these properties depend on the structure and therefore on the isomer composition of the substances used.

There are qualitative rules for the dependence of performance on structure. For example, Alan S. Wilson, Plasticizers, The Institute of Materials, 1995, ISBN 0 901716 76 6, pp. 135-136 discusses the properties of phthalates as a function of overall carbon number, i.e. of molar mass, and of degree of branching, i.e. of isomer composition, inter alia. At identical molar mass, for example, an increase in branching brings about, inter alia, Negative Effects
increasing viscosity
rising vapor pressure, therefore higher volatility
lower level of plasticizing action
lower resistance to heat and light
Positive Effects
better PVC compatibility
less migration
greater hydrolysis resistance
less biodegradation (during product use)
higher electrical resistance It is immediately apparent that there is no such thing as the best plasticizer, and a compromise has to be arrived at for each application. For example, if plasticizing action is of prime importance a plasticizer with the lowest possible level of branching will be preferred. In contrast, if the intention is to produce PVC cable sheathing use will preferably be made of products with a somewhat higher degree of branching, since they have better electrical insulating action.

Brian L. Wadey, Lucien Thil, Mo A. Khuddus, Hans Reich; The Nonyl Phthalate Ester and its Use in flexible PVC, Journal of Vinyl Technology, 1990, 12 (4), pp. 208-211 demonstrates very clearly with reference to some synthetically prepared single isomers of DINP how important properties depend on the structure of the esters.

In summary, it may be stated that performance depends on the structure of the phthalate, that this is partially dependent on the structure of the alcohol, and that this in turn is partially dependent on the structure of the underlying olefin. Another complicating factor is that these compounds are produced in the form of an isomer mixture. It would therefore be desirable to alter or formulate the composition of the mixture to obtain a mixture with prescribed properties.

The major difficulty is then that a wide variety of tests is needed to assess the performance suitability of the single substances. Taking phthalates as plasticizer for PVC as a simple example, a representative phthalate specimen first has to be prepared in the laboratory from the alcohol mixture available. Test plaques then have to be produced with PVC, frequently with two or more concentrations of plasticizer, the actual standardized tests are carried out on these. This is very complicated and takes days or weeks. For lubricant applications the resources required may be still greater and more expensive, for example if engine tests have to be run over a period of weeks.

Once a mixing specification has been developed, it then has to be ensured that a product with consistent properties is prepared in the production process. For example, the viscosity of lubricants has to be held within narrow limits in order to keep within the desired viscosity classification. Examples for plasticizers are that the plasticizing action has to remain constant so that processors using the plasticizer are not constantly forced to adjust the mixing specification, or that there is a minimum value for electrical resistance. As explained above, however, continuous production control via performance tests is currently not possible, irrespective of the costs which it would incur.

Although in theory it would be possible to solve the problem by keeping the isomer composition precisely constant, this is not achievable in practice. Crackers are not operated with the aim of supplying a constant-composition $C_4$ stream, but to produce ethylene, propylene, petroleum spirit, or other bulk products. In practice the composition of the $C_4$ stream available from the cracker will always vary depending on the composition of the raw material used and the mode of operation. The problem becomes even more intractable if $C_4$ streams are purchased from different crackers, as is generally the case for large-scale production.

The raw material used as a starting point in itself therefore inevitably causes changes in the composition of the product, and therefore changes in isomer distribution, and therefore changes in performance. As discussed above, other changes in product composition take effect in the subsequent steps of oligomerization and hydroformylation, for example through a change in operating conditions or aging of the oligomerization catalyst. The problem is most severe for independent ester producers who purchase the alcohols used, since the products can come from different oligomerization processes and oxo processes. Mention may be made again of the fact that there are DINP grades with viscosities of from ~50 to 170 mPa*s at 20° C., depending on the raw material, oligomerization process and hydroformylation process used in producing the isononanol used as esterification alcohol. The isolated example DINP demonstrates the fundamental problems, but similar considerations apply, of course, to all esters used as functional fluids, in particular where isomer mixtures of alcohols or carboxylic acids are used.

Although, as discussed above, it is possible in principle to use changes in isomer composition to tailor products for various application sectors, it is desirable for economic reasons to operate plants continuously. Even if we ignore the problem that the desired properties of the product have to be taken into account at the outset, it is very costly and time-consuming here to make frequent production changeovers to produce different product variants. The aim will therefore be to prepare a standard product with the most consistent properties possible, a product which covers the widest possible range of applications. However, customer requirements are becoming more stringent, and increasing customer-orientation requires a response to customers' wishes, and this response inevitably means the preparation of specific products alongside standard product.

Object

The object is therefore to prepare phthalate mixtures with certain properties from alcohol mixtures of very varied composition, where the properties of the phthalates can be controlled by simple means via the composition of the alcohols.

Ideally, a method should be found which permits the performance of the final products (phthalate mixtures) to be predicted before production of the critical precursors has been completed, e.g. during the hydroformylation of aldehydes produced from olefin isomer mixtures. This should be possible without lengthy performance tests on the final product (e.g. preparing the alcohols by hydrogenation and the carboxylic acids by oxidation, preparing the esters, producing test plaques using plasticized PVC, etc.).

Achievement of the Object

The viscosity of phthalate esters depends on the structure and, respectively, on the isomer composition of the alcohols used for esterification. This is correlated with performance variables, such as low-temperature flexibilizing action and electrical resistance. If sufficient measurements are available it can be described using theoretically based equations, or even simple empirical equations.

Measurement of the viscosity of the single phthalic esters, a particularly simple measurement, can therefore provide conclusions concerning other aspects of performance. The problem, however, is that this cannot be measured until the finished ester, for example DINP, becomes available. It is then too late to influence alcohol composition.

In principle, the viscosity of mixtures of isomer compounds can be estimated from the single components, using a simple mixing rule. The VDI-Wärmeatlas [VDI heat atlas], VDI Verlag, seventh extended edition, 194, section Da 30 states that $$\ln(\eta) = \Sigma x_e * \ln(\eta_e)$$

where $\eta$ viscosity of mixture
$\eta_e$ viscosity of single components (phthalates)
$x_e$ molar fraction of single component (phthalates)

Determination of the viscosity of the single components (phthalates) and measurement of the isomer composition (phthalates) would therefore be a suitable means for checking that product properties are kept constant. However, this is not possible in practice due to the enormous number of isomers, since the costs for testing these following their synthesis or isolation from reaction mixtures would be unacceptable using currently available means.

The following list gives the most important isomers of an isononanol used for preparing DINP and prepared by an oxo reaction of an octene mixture, in turn prepared by oligomerizing 2-butene. The composition can essentially be stated as follows, and has 14 isomers, ignoring stereoisomers: n-nonanol, 2-methyloctanol, 2-ethylheptanol, 2-propylhexanol, 4-methyloctanol, 3-ethylheptanol, 6-methyloctanol, 2,3-dimethylheptanol, 2-propyl-3-methylpentanol, 2-ethyl4-methylhexanol, 2,5-dimethylheptanol, 4,5-dimethylheptanol, 2,3,4-trimethylhexanol, and 2-ethyl-3-methylhexanol.

If the raw material initially used also comprises isobutene, for example, there are many additional isomers, such as 3,5,5,-trimethylhexanol, 3,4,5-trimethylhexanol, and 3,4,4-trimethylhexanol, and others.

When alcohols are esterified using a dibasic polycarboxylic acid, such as phthalic acid, the only case in which one single compound is produced arises when the alcohol used is composed of one single isomer. For example, when phthalic acid is esterified using n-nonanol, di-n-nonyl phthalate is produced. In contrast, if the esterification alcohol is composed of two or more isomers, the products produced in the esterification of phthalic acid, for example, are phthalates in which the two alkyl radicals are identical or different. Thus when the abovementioned isononanol with 14 isomers is used 14 phthalates can be produced with identical alkyl groups and 91 (14*13/2) phthalates can be produced with two different alkyl groups. If stereoisomers are ignored, a total of 105 different phthalates can therefore be formed.

In the case of compounds such as the esters of trimellitic acid, which is tribasic, or pyromellitic acid, which is tetrabasic, the number of isomers rises enormously. Every one of the isomers will have to be tested, and the analytical separation alone here is complicated and time-consuming, and the production of suitable specimens for viscosity measurement even more so.

Surprisingly, it has now been found that the viscosity of isomer mixtures of this type of esters is correlated with the composition of the esterification alcohols used in the case of polycarboxylic esters and, respectively, with the composition of the carboxylic acids used to esterify polyols.

The mixing rule cited above cannot be employed for the viscosity of the esters, since it is not the true composition of the esters which is inserted but merely the composition of the esterification alcohols, and, respectively, carboxylic acids. The result is viscosity parameters of the single isomers as contribution to the viscosity of the ester mixture obtained by esterification with multiple isomers. These values naturally also include the effects of interaction of the single isomers in the esters.

It could not be foreseen that, if the molar fractions of the single alcohol components used in the alcohol mixture which would be obtained by esterifying the phthalate mixture are identical, an ester mixture composed solely of phthalates whose alkyl radicals are identical would have almost the same viscosity as a phthalate mixture in which, alongside phthalates having identical alkyl radicals, there are also phthalates having isomeric alkyl radicals.

In other words: if every isomer present in an alcohol mixture were isolated and esterified with phthalic acid, and if the various phthalates were then mixed in the ratio in which the alcohols were present in the alcohol mixture, the viscosity of the phthalate mixture obtained would be approximately the same as that of the mixture which would result from direct reaction of the alcohol mixture with phthalic acid.

This result is very surprising, since the number of phthalate isomers which can result during direct esterification of the alcohol mixture with phthalic acid is, as stated above, significantly higher than that which can result during the esterification of the single components followed by mixing in the specified ratio. This means that it is not the actual number of phthalate isomers in the phthalate mixture which is important, but the isomer composition of the underlying alcohol mixture.

The present invention therefore provides mixtures of isomeric dialkyl phthalates with a certain viscosity, prepared by esterifying phthalic acid or phthalic anhydride with a mixture of isomeric alkyl alcohols having a certain number of carbon atoms, wherein the viscosity of the phthalic ester mixture is adjusted via the composition of the isomeric alkyl alcohols and their viscosity parameters in accordance with formula I.

$$\ln(\eta) = \Sigma x_i * \ln(\eta_i) \quad \text{equation (I)}$$

where $\eta$=viscosity of dialkyl phthalate mixture
  $x_i$=molar fraction of an isomerically pure alcohol
  $\eta_i$=viscosity parameter of an isomerically pure alcohol in a dialkyl phthalate mixture.

The viscosities of the mixtures depend on the number of carbon atoms in the isomeric alkyl alcohols used for esterification. The viscosities or preferred ranges of the invention are the following:

| Number of carbon atoms in isomeric alkyl alcohol | Viscosity of dialkyl phthalate mixture in mPa * s (20° C.) | | |
|---|---|---|---|
| | inventive | preferred | particularly preferred |
| 4 | 19-44 | 19-44 | 19-44 |
| 5 | 24-50 | 24-50 | 24-50 |
| 6 | 28-80 | 28-70 | 28-60 |
| 7 | 33-100 | 33-70 | 33-65 |
| 8 | 39-130 | 39-110 | 39-100 |
| 9 | 45-200 | 45-165 | 45-120 |
| 10 | 52-400 | 52-330 | 52-200 |
| 11 | 61-400 | 61-380 | 61-350 |
| 12 | 66-400 | 66-380 | 66-350 |
| 13 | 70-400 | 70-380 | 70-350 |
| 14 | 74-400 | 74-380 | 74-350 |

If a mixture of isomeric dialkyl phthalates is prepared with a certain viscosity $\eta$ by mixing two dialkyl phthalate mixtures, where in the limiting case it is also possible to use isomerically pure phthalic esters instead of the mixtures, the mixture content of the two components can be calculated in accordance with formula II, if the molar fractions of the isomeric alcohols underlying the phthalate mixtures are known.

$$\ln(\eta) = a\Sigma x_{i1} * \ln(\eta_i) + (1-a)\Sigma x_{i2} * \ln(\eta_i) \quad \text{equation (II)}$$

where $\eta$=viscosity of dialkyl phthalate mixture after mixing of the two components
  $x_{i1}$=molar fraction of an isomer in alcohol mixture 1 which would result from saponification of phthalate mixture 1
  $x_{i2}$=molar fraction of an isomer in alcohol mixture 2 which would result from saponification of phthalate mixture 2
  $\eta_i$=viscosity parameter of an alcohol isomer
  a=proportion of phthalate mixture 1 in two-component mixture
  (1-a)=proportion of phthalate mixture 2 in two-component mixture
  (a/(1-a))=mixing ratio of the two components By analogy with formula II, calculation methods can be set up for the mixing of more than two phthalate mixtures. For example, the equation applicable for the viscosity of a phthalate mixture prepared from three phthalate mixtures is $$\ln(\eta) = a\Sigma x_{i1} * \ln(\eta_i) + b\Sigma x_{i2} * \ln(\eta_i) + c\Sigma x_{i3} * \ln(\eta_a) \quad \text{equation III}$$

where a+b+c=1
  and a, b, and c are the proportions of the three components in the entire mixture.

The present invention therefore also provides mixtures of isomeric dialkyl phthalates with a certain viscosity, prepared by mixing of isomerically pure dialkyl phthalates and/or of dialkyl phthalate mixtures, where the alkyl esters have the same carbon number and have a carbon number corresponding to their viscosity, wherein the mixture of isomeric dialkyl phthalates has a viscosity and composition in accordance with formula IV (equations II and III being special cases of the generally applicable equation IV).

$$\ln(\eta) = \sum_{j=1}^{j=n} \sum_{i=1}^{i=m} a_j \, x_{ij} \, \ln(\eta_i) \quad \text{equation (IV)}$$

$$\text{where } \sum_{j=1}^{n} a_j = 1 \quad 0 \le a_j \le 1$$

n=number of components in mixture
m=number of alcohol isomers underlying the final mixture
$\eta$=viscosity of dialkyl phthalate mixture after mixing the components
$x_{ij}$=molar fraction of a particular isomer i in alcohol mixture j which would result from saponification of phthalate mixture j
$\eta_i$=viscosity parameter of a particular alcohol isomer i
$a_j$=mixture content (proportion by weight) of a component j (phthalate mixture) in final product.

With regard to chain lengths and viscosity and preferred ranges thereof, the statements made above are again applicable.

Equations II-IV are also applicable to calculation of the mixture contents when the intention is to prepare an alcohol mixture from two or more alcohol mixtures (components) with different isomer composition (nature of isomers and also quantitative proportion) for the preparation of a phthalate mixture with specified viscosity.

The present invention also provides processes for preparing the mixtures mentioned of isomeric dialkyl phthalates with the viscosities mentioned by blending of the phthalic esters or of the alcohols prior to esterification.

Isononyl phthalates of the invention prepared from the alkyl alcohols having 9 carbon atoms may be obtained using a mixture of isomeric alkyl alcohols which is a mixture of nonanols prepared by mixing an isomerically pure nonanol or a nonanol mixture with n-nonanol.

As an alternative, it is possible to use a mixture of isomeric alkyl alcohols which is a mixture of nonanols prepared by mixing an isomerically pure nonanol or a nonanol mixture with 3,5,5-trimethylhexanol.

If phthalic esters are mixed, e.g. dinonyl phthalates, an isomerically pure dinonyl phthalate or a dinonyl phthalate mixture may be mixed with di(3,5,5-trimethylhexyl) phthalate or di(isononyl) phthalate.

Suitable blending of the ancillary components permits preparation of any of the products whose viscosity lies between these limits. The alcohols n-nonanol or 3,5,5-trimethylhexanol, for example, can be used to adjust the viscosities of DINP grades in the range from ~45 to ~110 mPa*s, in the first instance giving a product with good low-temperature flexibilizing action, and in the second case giving a product with less good low-temperature flexibilizing action but with increased electrical resistance.

Readily adjustable viscosity makes the phthalic ester mixtures of the invention very versatile in use, and they can be used as plasticizers for plastics, in particular PVC, as hydraulic fluid, as lubricant, or as a component in lubricants.

Determination of Viscosity Contributions from Single Components

Firstly, it will seldom be possible or desirable to analyze every isomer including all of the trace constituents, since this would dramatically increase costs. The procedure here is to take any unknown residue in total and treat it as a virtual component. If this unknown residue is not excessively large, e.g. less than 10%, or preferably less than 5%, the error is not unacceptably great. For example, a large number of measurements with unknown residues of a few % are covered by a tolerance of +/−2 mPa*s for the final product.

Secondly, there will also occasionally be problems with autocorrelation of isomers. If, for example, 2-propylhexanol is produced during the oxo reaction of internal n-octenes, there will also always be some content of 2-ethylheptanol and 2-methyloctanol present, resulting in a high level of autocorrelation of these isomers. If these isomers cannot be clearly differentiated even by other measures, such as distillation, these autocorrelated constituents are likewise taken together as a single component. The effect on accuracy here is very small, since if even the measures described cannot remove the autocorrelation, it will be even more strongly present in practical production systems. It is therefore fully acceptable and justified to treat two or more components of this type as a single component.

It is surprising that it is not necessary to separate all of the components in order to determine the fictive contributions to viscosity. Indeed, in the case of isononanol up to three or four components can be taken together without exceeding the permitted tolerance. On the other hand, accuracy can be improved as desired, at correspondingly high cost, if this is rendered essential by particularly stringent requirements. However, it is rarely necessary to incur this cost. In practice a compromise will be sought between cost and accuracy.

As soon as the base data have been determined a solution is available for keeping within the limits. Since the effect of the components is now known, changes to the composition and therefore to the expected properties can be undertaken during the preparation process itself. It is not important that the composition of the products is held precisely constant, and as has been explained this is industrially impossible or possible only at unacceptable cost. Rather, it is important that the performance of the final product is constant. In practice the procedure is to have components, isomer mixtures, or defined alcohols ready for use which deviate markedly from the desired value.

The term isomers used below is for compounds of the same empirical formula but different structure. Isomerically pure means that the ester or alcohol is composed solely of compounds of one isomer (stereoisomers being regarded in this context as one isomer), but impurities of other isomers usually present and/or resulting from industrial processes are ignored.

The inventive phthalates and processes for their preparation permit rapid and automatable control of production at the precursor stage, e.g. of the preparation of isononanol by hydroformylation of complex octene mixtures followed by hydrogenation of the hydroformylation products, the isoindex and the nature of branching in the isomers being maintained during hydrogenation of the aldehydes to give the corresponding alcohols, and conclusions can be reached concerning the properties of the final products to be produced therefrom, DINP plasticizers in the example. An example of a method of control is a process gas chromatograph coupled to automatic calculation of the expected viscosity of the plasticizers. This permits automatic monitoring not only of product quality but even of the performance of the expected final products, in this case monitoring the physical variable of viscosity. Since, however, this has systematic correlation with other aspects of performance, any important variable may in principle be controlled within specified limits. All that is needed here to carry out continuous control is a single determination of the measured values needed.

The procedure in practice is to prepare a series of different mixtures with the greatest possible difference in isomer composition. Here, the problem mentioned at the outset can be utilized systematically for solving the problem by, for example, using octene mixtures of different composition, e.g. commercially available olefins, such as 1-octene, 4-octene, 2-ethyl-1-hexene, or 2,4,4-trimethylpentenes (diisobutene). It is also possible to prepare isomer mixtures by dehydrating alcohols on acidic catalysts, e.g. dehydrating 2-octanol or 2-ethylhexanol. One way of preparing dimethylhexenes is acidic oligomerization of 1- and 2-butene. All of the synthetic routes to preparation of olefins may be utilized in order to obtain starting olefins which are as different as possible.

The olefins are then hydroformylated by various processes, e.g. using HPCo, HPRh, or ligand-modified Rh or Co catalysts. This gives a further differentiation of the isomer composition, even if the starting olefin used is the same. Hydrogenation then gives the desired alcohols, isononanols in the example, with a completely different isomer composition. Further differentiation can be achieved by careful distillation, obtaining isomer cuts with non-natural isomer distribution. Of course, it is also possible to utilize other synthetic methods for preparing alcohols and aldehydes.

Mention should be made of the fact that even at the stage of olefin feed to the hydroformylation it is possible to adjust the viscosity of the final product. For example, an auxiliary, e.g. 1-octene, or a mixture of octenes with low branching levels, may be added to lower the viscosity of the plasticizer subsequently to be prepared from the mixture, or else diisobutene or an octene mixture with a high level of branching may be added to increase the viscosity in an analogous manner. In each case, continuous analysis reveals the isomer distribution established during a hydroformylation step in the oxo process, and this can be converted by calculation to give the required amount of the auxiliary to be added. It also permits calculation of the composition of the isomer distribution modified by the feed, and also in turn permits calculation of the expected viscosity of the plasticizer to be prepared.

The composition of the various alcohol mixtures is determined. It is helpful here, but not essential, to know the structure of each single isomer. However, it is important that the isomers can be distinguished and that their ratio to one another can be determined. Since isomer composition is generally analyzed by gas chromatography, the isomers can be distinguished by their retention indices, if possible determined on two different columns.

The example of nonanol mixtures will be taken below for further illustration of the invention.

EXAMPLE 1

An example of the procedure for analysis of nonanol mixtures is as follows: The retention indices are based on n-alkanols, n-heptanol=700
n-octanol=800
n-nonanol=900

Since the measurements are carried out in temperature-programed mode of operation (see analysis conditions) the retention indices ($R_i$) of the nonanol isomers are calculated using retention times (RT) between those of n-octanol and n-nonanol in accordance with the following formula:

$$R_i = 800 + (RT_i - RT_{n\text{-}octanol}) \div (RT_{n\text{-}nonanol} - RT_{n\text{-}octanol}) * 100$$

| Capillary columns of length 60 m | |
|---|---|
| Stationary phases: | |
| polar column | polyethylene glycol 20M |
| nonpolar column | 95% polydimethylsiloxane/ 5% polydiphenylsiloxane |
| Carrier gas: | helium |
| Gas flow: | 1.5 ml/min |
| Initial temperature: | 60° C. |
| Final temperature: | 220° C. |
| Heating rate: | 2° C./min |

Table 1 lists the analysis of an isononanol mixture. As shown by analyses of some selected mixtures, it is sufficiently accurate to take % by area as equal to percent by weight.

TABLE 1

| Name | Ret. time min | net ret. time min | ret. index internal | Boiling point ° C. | % by area | % by weight |
|---|---|---|---|---|---|---|
| n-heptanol | 24.59 | 21.45 | 700 | | | |
| n-octanol | 30.7 | 27.56 | 800 | 194.4 | | |
| (4-M-iso-pr-pentanol) | 29.45 | 26.31 | 779 | | 0.3 | 0.3 |
| A-2-E-4-M-hexanol | 29.54 | 26.40 | 781 | | 1.5 | 1.5 |
| B-2-E-4-M-hexanol | 30.00 | 26.86 | 788 | | 1.5 | 1.5 |
| A-2,5-DM-heptanol | 30.83 | 27.69 | 802 | | 5.2 | 5.2 |
| B-2,5-DM-heptanol | 30.92 | 27.78 | 804 | | 5.4 | 5.4 |
| A-2-Pr-3-M-pentanol | 31.02 | 27.88 | 805 | | 0.31 | 0.31 |
| X A | 31.14 | 28.00 | 807 | | 0.09 | 0.09 |
| B-2-Pr-3-M-pentanol | 31.405 | 28.26 | 812 | | 0.35 | 0.35 |
| A-2,3,4-TM-hexanol | 32.79 | 29.65 | 835 | | 0.44 | 0.44 |
| 2-Pr-hexanol | 31.54 | 28.40 | 814 | | 1.9 | 1.9 |
| A-2,3-DM-heptanol | 32.125 | 28.98 | 824 | | 1.1 | 1.1 |
| 3-E-4-M-hexanol | 33.5 | 30.36 | 846 | | 4.4 | 3.9 |
| B-2,3-DM-heptanol | 32.7 | 29.56 | 833 | | 1.5 | 1.5 |
| 2-E-heptanol | 32.46 | 29.32 | 829 | | 2.2 | 2.2 |
| 2-M-octanol | 33.06 | 29.92 | 839 | | 4.2 | 4.2 |
| 3-E-heptanol | 33.66 | 30.52 | 849 | | 8.1 | 8.1 |
| A-4,5-DM-heptanol | 34.63 | 31.49 | 865 | | 7.1 | 7.1 |
| B-4,5-DM-heptanol | 34.74 | 31.60 | 867 | | 8.9 | 8.9 |
| 4-M-octanol | 34.12 | 30.98 | 857 | | 19.5 | 19.5 |
| 6-M-octanol | 34.91 | 31.77 | 870 | | 18.7 | 18.7 |
| n-nonanol | 36.74 | 33.60 | 900 | 213.5 | 7.3 | 7.3 |

Abbreviations
A and B = diastereomers which can be distinguished by gas chromatography on a column with a packing which is not optically active.
E = ethyl
M = methyl
DM = dimethyl
Pr = propyl
X = unknown compound The esters are then prepared from the various alcohol mixtures and important performance data are determined, especially viscosity. However, in the case of phthalate mixtures the viscosity of these may be determined and the underlying alcohol mixture can be obtained from them by saponification and analyzed. The mixing rule is then used for the viscosity, but instead of the inaccessible proportions of the ester isomers use is made of the much simpler and easily determinable isomer distribution of the alcohols, and the data sets are subjected to a non-linear regression calculation. This gives estimated fictive viscosity contributions of the single components.

This procedure is carried out for nonyl phthalate mixtures. Tables 2 a-f list the isomer distributions of 52 isononanol mixtures and the viscosities of the nonyl phthalates prepared from these. Diastereomers are taken together. Unknown isomers are regarded as a combined virtual component. Some mixtures comprise 3,5,5-trimethylhexanol in addition to the compounds listed in Table 1.

Taking the data sets listed in Table 2a-f and equation II the program (DataFit, OAKDALE Engineering, Version 5.1,) is used to set up a fictive contribution to viscosity (viscosity parameter) for each isononanol isomer (Table 2f, final column). This procedure can also be used for other nonyl phthalate mixtures having other underlying nonanol isomers or having these and other underlying nonanol isomers. The precision of the values given in the final column of Table 2f for the fictive contribution to viscosity may be increased as the number of data sheets rises.

The goal of nonlinear regression is to determine the best fit parameters for a model by minimizing a chosen merit function. Where nonlinear regression differs is that the model has a nonlinear dependence on the unknown parameters, and the process of merit function minimization is an iterative approach. The process is to start with some initial estimates and incorporates algorithms to improve the estimates iteratively. The new estimates then become a starting point for the next iteration. These iterations continue until the merit function effectively stops decreasing.

The nonlinear model to be fitted can be represented by:

$$y = y(x;a)$$

The merit function minimized in performing nonlinear regression has the following formula:

$$x^2(a) = \sum_{i=1}^{N} \left[\frac{y_i - y(x_i; a)}{\sigma_i}\right]^2$$

where $\sigma_1$, is the measurement error, or standard deviation of the $i^{-th}$ data point. As with linear regression, the sum of the squares of the distances between the actual data points and the regression line is minimized.

Nonlinear regression iterations proceed as follows:
1. Obtain initial estimates for all of the variables being fitted for in the model. These initial estimates can be obtained from linear regression, rules, or by examining the curve generated by the data points. For models built into DataFit, linear regression is used to obtain the initial estimates. For user defined models, either rules need to be created or the user must specify the initial estimates.
2. Compute the merit function by use of the initial estimates.
3. Using an algorithm, adjust the variables in order to improve the fit of the model to the data points. DataFit utilizes the Levenberg-Marquardt method. Models built into DataFit use analytical derivatives during the optimization process, user defined models use numerical derivatives unless the user specifies the analytical derivatives.
4. The merit function is again computed and it is compared to the previous iteration.
5. Steps 3 and 4 are repeated until there is essentially no change in the merit function.

The iterations are then ceased
6. The goodness of fit statistics is then calculated.

Nonlinear regression is a better method than linear regression, because, to start with, it is a much more general procedure. There are a very limited number of models that can be expressed in linear form without transforming the data. Also, the fact the data are transformed means that the fitting routine minimizes the merit function on the transformed data, not the actual data. This makes nonlinear regression more accurate. Nonlinear regression can also be applied to essentially any equation that defines the independent variable Y as a function of the independent variable(s) X and at least one parameter. This is what provides the capability of defining one's own regression models.

Most of the overhead associated with the Levenberg-Marquardt algorithm lies with calculating derivatives. The derivative of the model with respect to every parameter being fitted must be calculated at every data point a number of times during the solution process. This can be a time consuming process, especially if there are a large number of data points. For models built in to DataFit, the derivatives are calculated analytically. This is the best method, as the result is exact and there is no iterating involved in calculating the derivative itself. User defined models whose derivatives are specified by the user are also calculated this way. If the derivatives are not defined for a user defined model, the derivatives are calculated iteratively in the following manner:
1. Evaluate the function, offsetting the parameter by some (rather significant) small positive number:

f(x+h)

2. Again, evaluate the function, offsetting the parameter variable by the same small number negated:

f(x+h)

3. Evaluate the derivative approximation by $$f'(x) = \frac{f(x+h) - f(x-h)}{2h}$$

4. Estimate the extrapolation error.
5. Decrease h, and repeat steps 1 through 4. When the error reaches an acceptable level, stop and return the approximated derivative.

Note: It is typically not necessary to specify the derivatives for user defined regression models as the above derivative algorithm is very robust.

Some data obtained in an experiment may be more or less accurate than other data, for many reasons. The apparatus used to collect the data may be more accurate in certain ranges than others, some data may have been recorded incorrectly, etc. In these cases, it may be desirable to give more significance, or "weight" to data that is known to be more accurate. In addition, weighting may be used to bring the selected model closer to certain data points, even thought the Residual Sum of Squares may be worsened.

As shown above, the merit function minimized in performing nonlinear regression is the following:

$$x^2(a) = \sum_{i=1}^{N} \left[\frac{y_i - y(x_i; a)}{\sigma_i}\right]^2,$$

where $\sigma_i$, is the standard deviation of the $i_{th}$ data point. If the value chosen for $\sigma_i$ is constant for all data points, no weighting is performed as each data point has equal impact on the merit function. This is what is done in the following cases:

1. A choice is made not to display the standard deviation column when a new project is created.
2. All of the standard deviation points are equally specified (the same value).

With weighting, data points with larger standard deviations, or outliers, will have less impact on the merit function. Consider the following two data sets and plots, one weighted, one not weighted:

| Weighted | | | UnWeighted | |
|---|---|---|---|---|
| X | Y | StDev | X | Y |
| 0 | 1.0 | 0.997 | 0.0 | 1.0 |
| 51 | 2.18 | 0.523 | 51.0 | 2.18 |
| 102 | 0.46 | 0.081 | 102.0 | 0.46 |
| 154 | 0.092 | 0.014 | 154 | 0.092 |
| 205 | 0.015 | 0.002 | 205.0 | 0.015 |
| 256 | 0.0084 | 0.0005 | 256 | 0.0005 |

TABLE 2a

| | Sample number | | | | | | | | |
|---|---|---|---|---|---|---|---|---|---|
| | 1 | 2 | 3 | 4 | 5 | 6 | 7 | 8 | 9 |
| Isononyl isomers | Composition in % by weight | | | | | | | | |
| n-nonanol | 89.5 | 1.2 | 50.8 | 46.1 | 97.5 | 19.2 | 0.4 | 0 | 0 |
| 2-methyloctanol | 7.9 | 56.2 | 33.5 | 39.0 | 0 | 32.1 | 0 | 0 | 0.1 |
| 2-ethylheptanol | 1.1 | 24.4 | 9 | 8.8 | 0 | 24.4 | 0.1 | 0 | 0.5 |
| 2-propylhexanol | 0.3 | 16.6 | 4.7 | 3.8 | 0 | 21.6 | 0 | 0 | 0.8 |
| 4-methyloctanol | 0.3 | 0.2 | 0.5 | 0.7 | 0 | 0.2 | 1.1 | 6.7 | 0 |
| 2,3-dimethylheptanol | 0 | 0.2 | 0.1 | 0 | 0 | 0.2 | 0 | 0 | 0.1 |
| 3-ethylheptanol | 0.1 | 0.3 | 0.3 | 0.4 | 0 | 0.8 | 0 | 0.1 | 0 |
| 2-propyl-3-methylpentanol | 0 | 0 | 0 | 0 | 0 | 0 | 0 | 0 | 8.6 |

TABLE 2a-continued

| Isononyl isomers | Sample number | | | | | | | | |
|---|---|---|---|---|---|---|---|---|---|
| | 1 | 2 | 3 | 4 | 5 | 6 | 7 | 8 | 9 |
| | Composition in % by weight | | | | | | | | |
| 2-ethyl-4-methylhexanol | 0 | 0 | 0 | 0 | 0 | 0.3 | 0 | 0 | 52.0 |
| 2,5-dimethylheptanol | 0 | 0.3 | 0 | 0 | 0 | 0.5 | 0 | 0 | 35.7 |
| 6-methyloctanol | 0.4 | 0.1 | 0.5 | 0.7 | 0 | 0.2 | 97.5 | 90.1 | 0 |
| 4,5-dimethylheptanol | 0 | 0 | 0 | 0 | 0 | 0.2 | 0.1 | 2.2 | 0 |
| 2,3,4-trimethylhexanol | 0 | 0 | 0 | 0 | 0 | 0 | 0 | 0 | 0.3 |
| 3-ethyl-4-methylhexanol | 0 | 0 | 0 | 0 | 0 | 0 | 0 | 0 | 0 |
| 3,5,5-trimethylhexanol | 0 | 0 | 0 | 0 | 0 | 0 | 0 | 0 | 0 |
| Residue | 0.4 | 0.5 | 0.6 | 0.5 | 2.5 | 0.3 | 0.8 | 0.9 | 1.9 |
| Measured viscosity* | 47.6 | 83.9 | 57.6 | 59.5 | 45.6 | 74.3 | 62.5 | 63.0 | 148.0 |

TABLE 2b

| Isononyl isomers | Sample number | | | | | | | | |
|---|---|---|---|---|---|---|---|---|---|
| | 10 | 11 | 12 | 13 | 14 | 15 | 16 | 17 | 18 |
| | Composition in % by weight | | | | | | | | |
| n-nonanol | 0 | 0 | 0 | 0 | 0.1 | 0 | 0 | 0 | 0 |
| 2-methyloctanol | 0 | 0 | 0.2 | 0.1 | 0.3 | 0 | 0 | 1.0 | 3.6 |
| 2-ethylheptanol | 0 | 2.3 | 0.2 | 0 | 4.4 | 0 | 0.9 | 0.1 | 1.4 |
| 2-propylhexanol | 0 | 5.5 | 0.1 | 0 | 0.4 | 0 | 0 | 0 | 1.0 |
| 4-methyloctanol | 12.6 | 0.1 | 16.8 | 23.6 | 5.4 | 1.8 | 0.8 | 37.5 | 13.4 |
| 2,3-dimethylheptanol | 0 | 3.4 | 0.2 | 0 | 7.5 | 0.2 | 0.7 | 0 | 1.2 |
| 3-ethylheptanol | 0.3 | 0.1 | 0.9 | 1.3 | 3.1 | 0.7 | 0.3 | 5.6 | 8.7 |
| 2-propyl-3-methylpentanol | 0 | 3.2 | 0.1 | 0 | 2.5 | 0 | 0 | 0 | 3.2 |
| 2-ethyl-4-methylhexanol | 0 | 0.8 | 0 | 0 | 7.8 | 0.2 | 0.5 | 0 | 36.2 |
| 2,5-dimethylheptanol | 0.2 | 82.1 | 3.2 | 0 | 8.1 | 0.7 | 0.4 | 0 | 7.1 |
| 6-methyloctanol | 79.2 | 0 | 67.1 | 61.7 | 1.4 | 1.4 | 0.5 | 28.2 | 1.2 |
| 4,5-dimethylheptanol | 6.2 | 0 | 10.0 | 13.1 | 27.1 | 55.7 | 66.6 | 26.7 | 14.0 |
| 2,3,4-trimethylhexanol | 0 | 2.2 | 0.2 | 0 | 15.8 | 2.8 | 3.6 | 0 | 0.4 |
| 3-ethyl-4-methylhexanol | 0 | 0 | 0.2 | 0.1 | 11.3 | 13.7 | 18.4 | 0.7 | 4.2 |
| 3,5,5-trimethylhexanol | 0 | 0 | 0 | 0 | 0 | 0.3 | 0 | 0 | 0 |
| Residue | 1.5 | 0.3 | 0.8 | 0.1 | 4.8 | 22.5 | 7.3 | 0.2 | 4.4 |
| Measured viscosity* | 65.6 | 125.0 | 66.5 | 65.8 | 140.0 | 116.0 | 110 | 70.6 | 112.0 |

TABLE 2c

| Isononyl isomers | Sample number | | | | | | | | |
|---|---|---|---|---|---|---|---|---|---|
| | 19 | 20 | 21 | 22 | 23 | 24 | 25 | 26 | 27 |
| | Composition in % by weight | | | | | | | | |
| n-nonanol | 10.1 | 0 | 7.5 | 0 | 8.6 | 3.6 | 3.4 | 3.4 | 5.8 |
| 2-methyloctanol | 5.0 | 1.8 | 3.8 | 2.4 | 4.6 | 8.4 | 1.6 | 1.7 | 0.6 |
| 2-ethylheptanol | 2.6 | 0.2 | 2.2 | 0.3 | 2.4 | 5.3 | 1.1 | 1.2 | 0.3 |
| 2-propylhexanol | 2.3 | 0 | 1.8 | 0.1 | 2.1 | 5.4 | 0.8 | 0.9 | 0.2 |
| 4-methyloctanol | 20.7 | 38.2 | 19.7 | 38.2 | 19.6 | 11.3 | 23.8 | 22.4 | 27.7 |
| 2,3-dimethylheptanol | 2.7 | 0.1 | 2.5 | 0.2 | 2.2 | 8.0 | 3.1 | 2.8 | 0.3 |
| 3-ethylheptanol | 8.5 | 8.3 | 8.2 | 9.9 | 8.1 | 5.0 | 9.3 | 8.9 | 6.7 |
| 2-propyl-3-methylpentanol | 0.7 | 0 | 0.4 | 0 | 0.2 | 1.2 | 0.3 | 0.3 | 0.1 |
| 2-ethyl-4-methylhexanol | 3.1 | 0 | 3.0 | 0 | 2.8 | 9.1 | 2.8 | 2.9 | 0.6 |
| 2,5-dimethylheptanol | 10.3 | 0 | 10.4 | 0.1 | 9.5 | 20.1 | 7.1 | 8.0 | 2.7 |
| 6-methyloctanol | 20.6 | 19.8 | 19.0 | 14.6 | 20.3 | 7.5 | 15.0 | 15.2 | 21.8 |
| 4,5-dimethylheptanol | 5.8 | 30.1 | 16.0 | 31.5 | 13.5 | 9.5 | 23.6 | 24.2 | 28.1 |
| 2,3,4-trimethylhexanol | 1.7 | 0 | 0.7 | 0 | 0.7 | 1.9 | 1.2 | 1.2 | 0 |
| 3-ethyl-4-methylhexanol | 0.5 | 1.3 | 3.7 | 2.1 | 3.4 | 2.3 | 6.1 | 6.6 | 3.6 |
| 3,5,5-trimethylhexanol | 0.3 | 0 | 0 | 0 | 0 | 0 | 0 | 0 | 0 |
| Residue | 5.1 | 0.2 | 1.1 | 0.6 | 2.0 | 1.4 | 0.8 | 0.3 | 1.5 |
| Measured viscosity* | 72.4 | 71.3 | 76.0 | 73.5 | 75.0 | 95.0 | 80.0 | 80.5 | 73.0 |

TABLE 2d

| Isononyl isomers | Sample number | | | | | | | | |
|---|---|---|---|---|---|---|---|---|---|
| | 28 | 29 | 30 | 31 | 32 | 33 | 34 | 35 | 36 |
| | Composition in % by weight | | | | | | | | |
| n-nonanol | 2.9 | 6.1 | 4.0 | 0 | 5.2 | 5.4 | 0 | 4.7 | 5.1 |
| 2-methyloctanol | 8.2 | 3.0 | 1.9 | 3.8 | 3.3 | 3.0 | 4.6 | 3.1 | 2.9 |
| 2-ethylheptanol | 7.0 | 2.2 | 1.3 | 0.7 | 2.2 | 1.4 | 1.1 | 2.2 | 3.0 |
| 2-propylhexanol | 5.3 | 2.0 | 1.0 | 0.2 | 2.1 | 1.5 | 0.4 | 2.2 | 1.4 |
| 4-methyloctanol | 7.7 | 16.6 | 21.2 | 36.3 | 14.7 | 16.6 | 34.4 | 13.8 | 14.7 |
| 2,3-dimethylheptanol | 10.0 | 2.6 | 3.2 | 0.5 | 2.6 | 2.4 | 1.0 | 2.6 | 4.9 |
| 3-ethylheptanol | 4.8 | 6.8 | 8.3 | 12.6 | 6.2 | 5.6 | 13.6 | 5.9 | 6.1 |
| 2-propyl-3-methylpentanol | 2.2 | 0.9 | 0.4 | 0 | 1.0 | 0 | 0 | 1.1 | 1.3 |
| 2-ethyl-4-methylhexanol | 9.0 | 4.7 | 2.6 | 0 | 5.9 | 2.7 | 0 | 6.5 | 4.5 |
| 2,5-dimethylheptanol | 19.8 | 12.1 | 8.5 | 0.2 | 13.3 | 11.7 | 0.4 | 13.9 | 9.5 |
| 6-methyloctanol | 6.3 | 15.7 | 14.8 | 9.0 | 13.7 | 18.0 | 7.5 | 12.7 | 12.9 |
| 4,5-dimethylheptanol | 9.0 | 16.9 | 24.6 | 32.3 | 17.8 | 15.6 | 31.3 | 18.4 | 19.4 |
| 2,3,4-trimethylhexanol | 1.8 | 1.2 | 1.2 | 0.1 | 1.0 | 0.6 | 0.2 | 0.9 | 5.7 |
| 3-ethyl-4-methylhexanol | 6.0 | 6.2 | 5.5 | 3.7 | 7.0 | 3.6 | 4.9 | 7.7 | 6.5 |
| 3,5,5-trimethylhexanol | 0 | 0 | 0 | 0 | 0 | 4.0 | 0 | 0 | 0 |
| Residue | 0 | 3.0 | 1.5 | 0.6 | 4.0 | 7.9 | 0.6 | 4.3 | 2.1 |
| Measured viscosity* | 98.0 | 82.6 | 80.8 | 75.2 | 86.7 | 87.1 | 76.4 | 91.7 | 94.7 |

TABLE 2e

| Isononyl isomers | Sample number | | | | | | | | |
|---|---|---|---|---|---|---|---|---|---|
| | 37 | 38 | 39 | 40 | 41 | 42 | 43 | 44 | 45 |
| | Composition in % by weight | | | | | | | | |
| n-nonanol | 4.0 | 9.2 | 0 | 0.4 | 0 | 0 | 0 | 0 | 0 |
| 2-methyloctanol | 1.5 | 10.2 | 6.9 | 1.6 | 9.7 | 14.0 | 8.2 | 16.0 | 14.9 |
| 2-ethylheptanol | 1.1 | 5.0 | 2.4 | 2.1 | 4.4 | 6.9 | 16.0 | 8.1 | 11.1 |
| 2-propylhexanol | 0.9 | 3.8 | 1.1 | 2.6 | 2.7 | 4.8 | 10.5 | 5.5 | 6.5 |
| 4-methyloctanol | 19.7 | 10.1 | 28.1 | 5.5 | 15.4 | 4.7 | 0.1 | 2.3 | 0.7 |
| 2,3-dimethylheptanol | 1.9 | 6.0 | 2.2 | 2.8 | 4.7 | 7.7 | 18.0 | 8.8 | 11.1 |
| 3-ethylheptanol | 7.5 | 4.2 | 16.6 | 3.0 | 19.0 | 18.0 | 1.7 | 11.0 | 7.0 |
| 2-propyl-3-methylpentanol | 0.4 | 1.5 | 0 | 1.2 | 0.1 | 0.3 | 0.6 | 0.3 | 0.5 |
| 2-ethyl-4-methylhexanol | 2.1 | 6.2 | 0 | 11.6 | 0.1 | 0.2 | 0.3 | 0.2 | 0.3 |
| 2,5-dimethylheptanol | 5.8 | 15.8 | 1.8 | 19.6 | 5.6 | 11.1 | 19.5 | 12.8 | 15.4 |
| 6-methyloctanol | 14.4 | 7.4 | 2.3 | 3.4 | 0.2 | 0.2 | 0.3 | 0.2 | 0.2 |
| 4,5-dimethylheptanol | 21.5 | 13.7 | 29.2 | 22.4 | 22.1 | 9.5 | 0.3 | 5.2 | 1.7 |
| 2,3,4-trimethylhexanol | 0.8 | 2.5 | 0.7 | 2.0 | 2.5 | 3.2 | 3.5 | 4.4 | 2.9 |
| 3-ethyl-4-methylhexanol | 4.5 | 3.6 | 8.7 | 12.7 | 12.6 | 18.0 | 18.9 | 23.0 | 27.3 |
| 3,5,5-trimethylhexanol | 0.5 | 0 | 0 | 0 | 0 | 0 | 0 | 0 | 0 |
| Residue | 13.4 | 0.8 | 0 | 9.1 | 0.9 | 1.4 | 2.1 | 2.2 | 0.4 |
| Measured viscosity* | 88.0 | 89.7 | 80.2 | 114.0 | 85.9 | 93.4 | 115.0 | 101.0 | 104 |

TABLE 2f

| Isononyl isomers | Sample number | | | | | | | Fictive contribution to viscosity of isomers |
|---|---|---|---|---|---|---|---|---|
| | 46 | 47 | 48 | 49 | 50 | 51 | 52 | |
| | Composition in % by weight | | | | | | | |
| n-nonanol | 0 | 7.8 | 99.4 | 0 | 44.4 | 4.7 | 4.7 | 45.5 |
| 2-methyloctanol | 0 | 4.2 | 0 | 0 | 2.5 | 2.5 | 2.6 | 72.2 |
| 2-ethylheptanol | 0 | 2.2 | 0 | 0 | 1.3 | 1.3 | 1.3 | 98.7 |
| 2-propylhexanol | 0 | 1.9 | 0 | 0 | 1.1 | 1.1 | 1.1 | 98.7 |
| 4-methyloctanol | 0 | 20.5 | 0 | 0 | 12.3 | 12.3 | 11.5 | 67.2 |
| 2,3-dimethylheptanol | 0 | 2.6 | 0 | 0 | 1.6 | 1.6 | 1.4 | 108.4 |
| 3-ethylheptanol | 0 | 8.4 | 0 | 0 | 5.0 | 5.0 | 4.5 | 50.5 |
| 2-propyl-3-methylpentanol | 0 | 0.7 | 0 | 0 | 0.4 | 0.4 | 0.4 | 229.5 |
| 2-ethyl-4-methylhexanol | 0 | 2.8 | 0 | 0 | 1.7 | 1.7 | 1.7 | 158.4 |
| 2,5-dimethylheptanol | 0 | 10.2 | 0 | 0 | 6.1 | 6.1 | 6.4 | 120.2 |
| 6-methyloctanol | 0 | 19.9 | 0 | 0 | 11.9 | 11.9 | 11.1 | 61.1 |
| 4,5-dimethylheptanol | 0 | 13.7 | 0 | 0 | 8.2 | 8.2 | 7.7 | 94.4 |
| 2,3,4-trimethylhexanol | 0 | 0.5 | 0 | 0 | 0.3 | 0.3 | 0.3 | 574.3 |
| 3-ethyl-4-methylhexanol | 0 | 3.5 | 0 | 0 | 2.1 | 2.1 | 1.9 | 120.6 |
| 3,5,5-trimethylhexanol | 97.5 | 0 | 0 | 99.8 | 0 | 39.9 | 42.5 | 111.8 |
| Residue | 2.5 | 1.1 | 0 | 0.2 | 0.9 | 0.7 | 0.9 | (173.1) |
| Measured viscosity* | 113.0 | 76.4 | 43.8 | 111.9 | 61.2 | 89.0 | 90.6 | |

EXAMPLE 2

Variants of Process for Preparing Diisononyl Phthalate (DINP) by Esterifying Phthalic Anhydride with a Mixture of Isomeric Nonanols The DINP to be prepared is to have a viscosity of about 78 mPa*s with limits 75-80 mP*s. A contribution of n-nonanol to the overall viscosity is about 43 mPa*s and that of 3,5,5-trimethylhexanol is about 111 mPa*s.

If the DINP viscosity calculated from the isomer distribution of the isononanol prepared rises above a set limit, e.g. above 80 mPa*s, n-nonanol is added during the esterification in such a way as to regain the selected value, i.e. 78 mPa*s in the example. If the calculated viscosity falls below a selected limit, for example below 75 mPa*s, 3,5,5-trimethylhexanol, which increases the viscosity, is simply added during the esterification until the desired value has been regained. By analogy with admixture of the alcohol to the esterification, the same effect can be achieved by mixing the esters.

In both cases, use can be made of equation II, and since the second component used is a pure isomer the equation assumes the following form:

$$\ln(\eta) = a\Sigma x_{i1} * \ln(\eta_i) + (1-a) * \ln(\eta_i)$$

where $\eta$=viscosity of dialkyl phthalate mixture after mixing of the two components $x_{i1}$=molar fraction of an isomer in alcohol mixture 1 which would result from saponification of phthalate mixture 1

$x_{i2}$=molar fraction of an isomer in alcohol mixture 2 which would result from saponification of phthalate mixture 2

$\eta_i$=viscosity parameter of an alcohol isomer a=proportion of phthalate mixture 1 in two-component mixture (1-a)=proportion of the pure phthalate in two-component mixture (a/(1-a)=mixing ratio of the two components)

With the aid of this equation it is possible to calculate the mixture contents of the two components.

n-Nonanol is available commercially, but it is also possible to hydroformylate commercially available 1-octene or, at lower cost, internal n-octenes to give an isomer mixture with low contribution to the viscosity, which merely has to be markedly below the selected limit. 3,5,5-Trimethylhexanol is also available commercially and may also be prepared in a simple manner by hydroformylating diisobutene followed by hydrogenation. Diisobutene in turn is available via oligomerization of isobutene, and is a commercially available product. Finally, isomer mixtures with low and high contribution to viscosity may be held available. EP 1 029 839 shows how an isononanol which gives a viscosity of 77 mPa*s in DINP is obtained from an octene mixture. It also appears that it is possible to break down the octene mixture into two fractions with relatively low and relatively high degrees of branching. After an oxo reaction, hydrogenation to give the alcohols, and subsequent esterification with phthalic anhydride the lower-branched fraction gives a DINP with about 68 mPa*s, while the higher-branched fraction gives a DINP with about 103 mPa*s. For the process described, it is therefore sufficient for these two alcohol fractions, which derive from the same raw material as the isononanol produced, to be held available.

The following examples describe the relationship between differing-isomer-composition DINP mixtures and the viscosity and performance of these.

EXAMPLE 3

Preparation of Dinonyl Phthalate Mixtures (DINP)

148 g of phthalic anhydride (1 mol), 432 g of a nonanol mixture (3 mol, i.e. 50% excess), and 0.5 g of tetra-n-butyl titanate were charged to a distillation flask equipped with water separator and high-performance condenser, and heated slowly to boiling, with stirring. Esterification proceeded at atmospheric pressure with reflux of the alcohol charge, and the water of reaction produced here was successively removed at the water separator. Esterification was continued to an acid value <0.3 mg KOH/g. The alcohol was then distilled off in vacuo. For neutralization, the crude ester was cooled to 80° C. and stirred for about 30 minutes at atmospheric pressure after addition of the appropriate amount of sodium hydroxide solution. The organic phase was then washed repeatedly with water, and the aqueous phase was then removed.

The ester was then heated in vacuo to 180° C. Deionized water (8% based on the starting weight of crude ester) was added dropwise at constant temperature by way of an immersion tube. Once this steam distillation had ended, a reduced pressure of 30 mbar was applied for 30 minutes at 180° C. to remove traces of water. The product was then cooled in vacuo to 80° C. and was then filtered through a suction funnel, using filter paper and filtering aids.

EXAMPLE 4

Determination of Glass Transition Temperatures

The dynamic viscosity of the resultant nonyl phthalate is then determined at 20° C. to DIN 53015, as is, where appropriate, the glass transition temperature $T_g$, which is a measure of the flexibilizing action of a plasticizer. The lower the $T_g$ of the pure plasticizer, the lower the $T_g$ of the plasticized PVC produced therewith at a given mixing ratio, and therefore the higher its flexibility.

An example of a method of determining $T_g$ is differential scanning calorimetry (DSC) or torsional braid analysis (TBA). In the cases described here the TBA method was used for greater accuracy. The method was a variant of the "traditional" torsional oscillation analysis (TOA) described in DIN EN ISO 6721 Part 2, for example. In TBA the material to be tested (here the plasticizer) was applied (loading between 18 and 25% by weight) to a desized glass fiber roving in the form of a braid. The stiffness G' and the loss modulus G" were determined for each of these at temperatures of from −180° C. to +100° C., at frequency 1 s$^{-1}$ in the torsion-pendulum test (MYRENNE ATM III). The glass transition temperature $T_g$ could be determined from the maximum of G".

Relationship Between Glass Transition Temperature and Viscosity of DINP

Various nonanol mixtures were used to prepare the corresponding diisononyl phthalates, and the viscosity and glass transition temperature of the plasticizer (phthalate) were determined. The table below lists the relevant data.

| Specimen | Viscosity at 20° C. in mPa * s | $T_g$ in ° C. |
|---|---|---|
| A | 57.6 | −84.1 |
| B | 59.5 | −84.4 |
| C | 62.5 | −86 |
| D | 73 | −82.6 |
| E | 74.3 | −81.9 |
| F | 78 | −81.7 |
| G | 81 | −82 |
| H | 83.9 | −81.3 |
| I | 87.1 | −79.5 |
| J | 89.7 | −79.3 |
| K | 98 | −78.3 |
| L | 110 | −76.7 |
| M | 128 | −73.4 |
| N | 170 | −65.3 |

Practically linear dependence of the viscosity on glass transition temperature is found. The correlation factor is 0.99 (MICROSOFT EXCEL®, "KORREL"® statistical function).

EXAMPLE 5

Glass transition temperature of plasticizer—glass transition temperature of plasticized PVC relationship for DINP Pressed plaques of plasticized PVC were processed as specified below using some of the abovementioned nonanol mixtures esterified to give phthalates:

700 g of suspension PVC with K value 70 (e.g. VESTOLIT S 7054®) were mixed with 300 g of the plasticizer, and also 21 g of a dibasic lead phthalate PEBETAL® and 2.1 g of a neutral lead stearate BAROSTAB PB 28 F®, and processed at temperatures of up to 120° C. to give a dry blend(heated mixer). The mixture was then cooled. To produce milled sheets, 250 g of the resultant dry blend were placed on a Schwabenthan model 1133/0578 roll mill (roll gap 1.2 mm, roll temperature 165° C.). Once the milled sheet had formed, plastification continued for a total of 5 more minutes. Once the milled sheet had been removed from the roll mill and cooled, pieces (about 80 g) were cut out from the milled sheet, placed into a 220*220*1 mm template, and pressed as follows in a Werner & Pfleiderer hydraulic hand press (60 t): the temperature was set to 170° C. and the template with milled sheet first pressed for 2 min. at 50 bar, then 1 min. at 100 bar and finally again 2 min. at 180 bar. The pressure was then increased to 200 bar and cooling to room temperature took place at this temperature.

| Specimen | Viscosity | $T_g$ of plasticizer | $T_g$ of plasticized PVC |
|---|---|---|---|
| A | 57.6 | −84.1 | −29.1 |
| B | 59.5 | −84.4 | −27.8 |
| E | 74.3 | −81.9 | −24.4 |
| H | 83.9 | −81.3 | −23.9 |
| K | 98 | −78.3 | −19.6 |

If the glass transition temperatures of the pure plasticizers are plotted against the glass transition temperatures of the plasticized PVC plaques prepared from them, here again a clear correlation is found with a coefficient of 0.98.

The correlation coefficient between viscosity of the plasticizer and the performance variable of glass transition temperature of the plasticized PVC plaque can be calculated as 0.98. (MICROSOFT EXCEL®, "KORREL" statistical function).

Examples 3-5 are evidence that the plasticizing action of DINP correlates with its viscosity, determined by the isomer composition of the underlying nonanol mixture.

EXAMPLE 6

Relationship Between Glass Transition Temperature and Viscosity for Didecyl Phthalates (DIDP)

The aldehydes n-valeraldehyde ("1"), 2-methylbutanal ("2"), and 3-methylbutanal ("3") can be produced by hydroformylating 1-butene, 2-butene, or isobutene. Depending on which of these aldehydes (or else a mixture thereof) is used as starting material for the subsequent aldol condensation and hydrogenation to give the corresponding $C_{10}$ alcohols, various different homo- and/or coaldol condensates can be produced.

As described for nonanol, the $C_{10}$ alcohols were reacted to give the corresponding phthalate mixtures (DIDP) and analyzed.

In the list below, the viscosities and glass transition temperatures are listed for some phthalic esters prepared from these $C_{10}$ alcohols. GC and NMR were used to determine the following compositions, for which the following abbreviated terms have been used:

| Chemical name | Abbreviated form |
|---|---|
| 2-isopropyl-5-methyl-1-hexanol | 3 + 3 |
| 2-isopropyl-4-methyl-1-hexanol (2 diastereomers) | 2 + 3 |
| 2-propyl-5-methyl-1-hexanol/ 2-isopropyl-1-heptanol | 1 + 3 |
| A-2-propyl-4-methyl-1-hexanol (2 diastereomers) | 1 + 2 |
| 2-propyl-1-heptanol | 1 + 1 |

Composition and physical data for various $C_{10}$ phthalates based on coaldol:

| Specimen | 1 + 1 | 1 + 2 | 1 + 3 | 3 + 2 | 3 + 3 | Residue | Viscosity in mPa * s | Glass transition temperature in ° C. |
|---|---|---|---|---|---|---|---|---|
| AA | 98.8% | 0 | 0 | 0 | 0 | 1.2% | 118 | −76.8 |
| AB | 14.2% | 85.7% | 0 | 0 | 0 | 0.1% | 201 | −69.9 |

-continued

| Specimen | 1 + 1 | 1 + 2 | 1 + 3 | 3 + 2 | 3 + 3 | Residue | Vis-cosity in mPa*s | Glass transi-tion temperature in °C. |
|---|---|---|---|---|---|---|---|---|
| AC | 7.0% | 0 | 72.3% | 0 | 16.5% | 4.2% | 189 | −69.5 |
| AD | 0 | 0 | 0 | 0 | 99.6% | 0.4% | 313 | −62.7 |
| AE | 0 | 0 | 0 | 70.6% | 29.2% | 0.2% | 368 | −63.3 |
| AF | 29.0% | 57.5% | 3.0% | 3.7% | 5.8% | 1.0% | 176 | −72.3 |

If the viscosity of the $C_{10}$ phthalates here is likewise plotted against the glass transition temperature in °C., here again a clear correlation results (Korrel function, correlation factor 0.95).

EXAMPLE 6

Adjustment of DINP to Required Values, e.g. 70, 80, 90 mPa*s by Blending

Isononanol was mixed in the ratio given in the table with n-nonanol or 3,5,5-trimethylhexanol and reacted as described above to give the corresponding phthalates.

| Speci-men | Alcohol used | Model viscosity | Experimental viscosity | Deviation from model |
|---|---|---|---|---|
| O | isononanol (INA) | 76.4 | 75.2 | 1.6% |
| P | n-nonanol (n-C9) | 43.8 | 45.8 | 4.5% |
| Q | 3,5,5-trimethylhexanol (TMHol) | 111.9 | 109 | 2.6% |
| R | INA:n-C9 = 85:15 | 70 | 69 | 1.4% |
| S | INA:n-C9 = 50:50 | 58 | 56.9 | 1.9% |
| T | INA:n-C9 = 75:25 | 66.5 | 64.3 | 3.3% |
| U | INA:TMHol = 80:20 | 82.5 | 80.6 | 2.3% |
| V | INA:TMHol = 50:50 | 92.5 | 89.2 | 3.8% |
| W | INA:TMHol = 70:30 | 85.7 | 83.2 | 2.9% |

If the isononanol isomer distribution used as a starting point was one for which the model calculates a viscosity of 76 mPa*s (specimen O) and if a customer needs a specific DINP grade of about 70 mPa*s, the calculation model determined that about 15% of n-nonanol would have to be admixed prior to esterification.

The viscosities predicted by the model were in good agreement (<5% deviation) with the values obtained experimentally.

What is claimed is:

1. A process for preparing a mixture of isomeric dialkyl phthalates having a desired viscosity, which comprises:
   esterifying phthalic acid or phthalic anhydride with a mixture of isomeric alkyl alcohols having a certain number of carbon atoms, wherein the molar fraction of each alkyl alcohol isomer of an isomeric alcohol mixture is determined and wherein the viscosity parameter of each alkyl alcohol isomer of the mixture, which, upon reacting with phthalic acid or phthalic anhydride, results in a mixed isomer dialkyl phthalate ester product having a specific desired viscosity, is determined in accordance with formula (I):

$$\ln(\eta) = \Sigma \chi_i * \ln(\eta_i) \quad (I)$$

where $\eta$ = the calculated viscosity of a dialkyl phthalate mixture,
   $\chi_i$ = the molar fraction of an isomerically pure alcohol (i), and
   $\eta_i$ = the calculated viscosity parameter of isomerically pure alcohol (i).

2. The process as claimed in claim 1, wherein a mixture of isomeric dialkyl phthalates with a viscosity ranging from 19 to 44 mPa*s is prepared by esterifying phthalic acid or phthalic anhydride with a mixture of isomeric alkyl alcohols having 4 carbon atoms, and the viscosity of the phthalic ester mixture is adjusted via the composition of the isomeric alkyl alcohols and their viscosity parameters in accordance with formula (I).

3. The process as claimed in claim 1, wherein a mixture of isomeric dialkyl phthalates with a viscosity ranging from 24 to 50 mPa*s is prepared by esterifying phthalic acid or phthalic anhydride with a mixture of isomeric alkyl alcohols having 5 carbon atoms, and the viscosity of the phthalic ester mixture is adjusted via the composition of the isomeric alkyl alcohols and their viscosity parameters in accordance with formula (I).

4. The process as claimed in claim 1, wherein a mixture of isomeric dialkyl phthalates with a viscosity ranging from 28 to 80 mPa*s is prepared by esterifying phthalic acid or phthalic anhydride with a mixture of isomeric alkyl alcohols having 6 carbon atoms, and the viscosity of the phthalic ester mixture is adjusted via the composition of the isomeric alkyl alcohols and their viscosity parameters in accordance with formula (I).

5. The process as claimed in claim 1, wherein a mixture of isomeric dialkyl phthalates with a viscosity ranging from 33 to 100 mPa*s is prepared by esterifying phthalic acid or phthalic anhydride with a mixture of isomeric alkyl alcohols having 7 carbon atoms, and the viscosity of the phthalic ester mixture is adjusted via the composition of the isomeric alkyl alcohols and their viscosity parameters in accordance with formula (I).

6. The process as claimed in claim 1, wherein a mixture of isomeric dialkyl phthalates with a viscosity ranging from 39 to 130 mPa*s is prepared by esterifying phthalic acid or phthalic anhydride with a mixture of isomeric alkyl alcohols having 8 carbon atoms, and the viscosity of the phthalic ester mixture is adjusted via the composition of the isomeric alkyl alcohols and their viscosity parameters in accordance with formula (I).

7. The process as claimed in claim 1, wherein a mixture of isomeric dialkyl phthalates with a viscosity ranging from 52 to 400 mPa*s is prepared by esterifying phthalic acid or phthalic anhydride with a mixture of isomeric alkyl alcohols having 10 carbon atoms, and the viscosity of the phthalic ester mixture is adjusted via the composition of the isomeric alkyl alcohols and their viscosity parameters in accordance with formula (I).

8. The process as claimed in claim 1, wherein a mixture of isomeric dialkyl phthalates with a viscosity ranging from 61 to 400 mPa*s is prepared by esterifying phthalic acid or phthalic anhydride with a mixture of isomeric alkyl alcohols having 11 carbon atoms, and the viscosity of the phthalic ester mixture is adjusted via the composition of the isomeric alkyl alcohols and their viscosity parameters in accordance with formula (I).

9. The process as claimed in claim 1, wherein a mixture of isomeric dialkyl phthalates with a viscosity ranging from 66 to 400 mPa*s is prepared by esterifying phthalic acid or phthalic anhydride with a mixture of isomeric alkyl alcohols having 12 carbon atoms, and the viscosity of the phthalic ester mixture is adjusted via the composition of the isomeric alkyl alcohols and their viscosity parameters in accordance with formula (I).

10. The process as claimed in claim 1, wherein a mixture of isomeric dialkyl phthalates with a viscosity ranging from 70 to 400 mPa*s is prepared by esterifying phthalic acid or phthalic anhydride with a mixture of isomeric alkyl alcohols having 13 carbon atoms, and the viscosity of the phthalic ester mixture is adjusted via the composition of the isomeric alkyl alcohols and their viscosity parameters in accordance with formula (I).

11. The process as claimed in claim 1, wherein a mixture of isomeric dialkyl phthalates with a viscosity ranging from 74 to 400 mPa*s is prepared by esterifying phthalic acid or phthalic anhydride with a mixture of isomeric alkyl alcohols having 14 carbon atoms, and the viscosity of the phthalic ester mixture is adjusted via the composition of the isomeric alkyt alcohols and their viscosity parameters in accordance with formula (I).

12. The process as claimed in claim 1, wherein a mixture of isomeric dialkyl phthalates with a viscosity ranging from 45 to 200 mPa*s is prepared by esterifying phthalic acid or phthalic anhydride with a mixture of isomeric alkyl alcohols having 9 carbon atoms, and the viscosity of the phthalic ester mixture is adjusted via the composition of the isomeric alkyl alcohols and their viscosity parameters in accordance with formula (I).

13. The process as claimed in claim 12, wherein the mixture of isomeric alkyl alcohols having 9 carbon atoms comprises a mixture of nonanols which is prepared by mixing an isomerically pure nonanol or a nonanol mixture with n-nonanol.

14. The process as claimed in claim 12, wherein the mixture of isomeric alkyl alcohols having 9 carbon atoms comprises a mixture of nonanols which is prepared by mixing an isomerically pure nonanol or a nonanol mixture with 3,5,5-trimethylhexanol.

15. A process for preparing mixtures of isomeric dialkyl phthalates, which comprises:
mixing isomerically pure dialkyl phthalates, whose alkyl moieties have the same number of carbon atoms, and in such amounts as to achieve a certain viscosity that is determined by equation IV:

$$\ln(\eta) = \sum_{j=1}^{j=n} \sum_{i=1}^{i=m} a_j \, x_{ij} \, \ln(\eta_i) \quad \text{(IV)}$$

$$\text{where } \sum_{j=1}^{n} a_j = 1 \quad 0 \leq a_j \leq 1$$

n=the number of components in the mixture,
m=the number of alcohol isomers from which the isomeric dialkyl phthalates of the mixture of dialkyl phthalate esters are formed,
η=the calculated viscosity of the dialkyl phthalate mixture after mixing the components,
$x_{ij}$=the molar fraction of a particular isomer i in an alcohol mixture which would result from saponification of phthalate mixture j,
$\eta_i$=the viscosity parameter of a particular alcohol isomer i, and
$a_j$=the mixture content (proportion by weight) of a component j (phthalate mixture) in the final product.

16. The process as claimed in claim 15, wherein a mixture of isomeric dialkyl phthalates with a viscosity ranging from 19 to 44 mPa*s is prepared by mixing isomerically pure dialkyl phthalates and/or dialkyl phthalate mixtures, where the esterifying alkyl groups contain 4 carbon atoms, and the mixtures of the isomeric dialkyl phthalates has a viscosity and composition in accordance with formula (IV).

17. The process as claimed in claim 15, wherein a mixture of isomeric dialkyl phthalates with a viscosity ranging from 24 to 50 mPa*s is prepared by mixing isomerically pure dialkyl phthalates and/or dialkyl phthalate mixtures, where the esterifying alkyl groups contain 5 carbon atoms, and the mixtures of the isomeric dialkyl phthalates has a viscosity and composition in accordance with formula (IV).

18. The process as claimed in claim 15, wherein a mixture of isomeric dialkyl phthalates with a viscosity ranging from 28 to 80 mPa*s is prepared by mixing isomerically pure dialkyl phthalates and/or dialkyl phthalate mixtures, where the esterifying alkyl groups contain 6 carbon atoms, and the mixtures of the isomeric dialkyl phthalates has a viscosity and composition in accordance with formula (IV).

19. The process as claimed in claim 15, wherein a mixture of isomeric dialkyl phthalates with a viscosity ranging from 33 to 100 mPa*s is prepared by mixing isomerically pure dialkyl phthalates and/or dialkyl phthalate mixtures, where the esterifying alkyl groups contain 7 carbon atoms, and the mixtures of the isomeric dialkyl phthalates has a viscosity and composition in accordance with formula (IV).

20. The process as claimed in claim 15, wherein a mixture of isomeric diaflcyl phthalates with a viscosity ranging from 39 to 130 mPa*s is prepared by mixing isomerically pure dialkyl phthalates and/or dialkyl phthalate mixtures, where the esterifying alkyl groups contain 8 carbon atoms, and the mixtures of the isomeric dialkyl phthalates has a viscosity and composition in accordance with formula (IV).

21. The process as claimed in claim 15, wherein a mixture of isomeric dialkyl phthalates with a viscosity ranging from 52 to 400 mPa*s is prepared by mixing isomerically pure dialkyl phthalates and/or dialkyl phthalate mixtures, where the esterifying alkyl groups contain 10 carbon atoms, and the mixtures of the isomeric dialkyl phthalates has a viscosity and composition in accordance with formula (IV).

22. The process as claimed in claim 15, wherein a mixture of isomeric dialkyl phthalates with a viscosity ranging from 61 to 400 mPa*s is prepared by mixing isomerically pure dialkyl phthalates and/or dialkyl phthalate mixtures, where the esterifying alkyl groups contain 11 carbon atoms, and the mixtures of the isomeric dialkyl phthalates has a viscosity and composition in accordance with formula (IV).

23. The process as claimed in claim 15, wherein a mixture of isomeric dialkyl phthalates with a viscosity ranging from 66 to 400 mPa*s is prepared by mixing isomerically pure dialkyl phthalates and/or dialkyl phthalate mixtures, where the esterifying alkyl groups contain 12 carbon atoms, and the mixtures of the isomeric dialkyl phthalates has a viscosity and composition in accordance with formula (IV).

24. The process as claimed in claim 15, wherein a mixture of isomeric dialkyl phthalates with a viscosity ranging from 70 to 400 mPa*s is prepared by mixing isomerically pure dialkyl phthalates and/or dialkyl phthalate mixtures, where the esterifying alkyl groups contain 13 carbon atoms, and the mixtures of the isomeric dialkyl phthalates has a viscosity and composition in accordance with formula (IV).

25. The process as claimed in claim 15, wherein a mixture of isomeric dialkyl phthalates with a viscosity ranging from 74 to 400 mPa*s is prepared by mixing isomerically pure dialkyl phthalates and/or dialkyl phthalate mixtures, where the esterifying alkyl groups contain 14 carbon atoms, and the mixtures of the isomeric dialkyl phthalates has a viscosity and composition in accordance with formula (IV).

26. The process as claimed in claim 15, wherein a mixture of isomeric dialkyl phthalates with a viscosity ranging from 45 to 200 mPa*s is prepared by mixing isomerically pure dialkyl phthalates and/or dialkyl phthalate mixtures, where the esterifying alkyl groups contain 9 carbon atoms, and the mixtures of the isomeric dialkyl phthalates has a viscosity and composition in accordance with formula (IV).

* * * * *